United States Patent
Heaton et al.

(10) Patent No.: US 9,561,312 B2
(45) Date of Patent: *Feb. 7, 2017

(54) REDUCED PRESSURE DELIVERY SYSTEM HAVING A MANUALLY-ACTIVATED PUMP FOR PROVIDING TREATMENT TO LOW-SEVERITY WOUNDS

(71) Applicant: KCI Licensing, Inc., San Antonio, TX (US)

(72) Inventors: Keith P. Heaton, Poole (GB); Ian James Hardman, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 172 days.

This patent is subject to a terminal disclaimer.

(21) Appl. No.: 14/172,732

(22) Filed: Feb. 4, 2014

(65) Prior Publication Data
US 2014/0155849 A1    Jun. 5, 2014

Related U.S. Application Data

(60) Continuation of application No. 13/205,807, filed on Aug. 9, 2011, now Pat. No. 8,679,079, which is a
(Continued)

(51) Int. Cl.
*A61M 1/00* (2006.01)
*A61M 3/02* (2006.01)
*A61M 27/00* (2006.01)

(52) U.S. Cl.
CPC .......... *A61M 1/0088* (2013.01); *A61M 1/0011* (2013.01); *A61M 1/0066* (2013.01);
(Continued)

(58) Field of Classification Search
CPC ...... A61M 1/00; A61M 27/00; A61M 1/0011; A61M 1/0088; A61M 1/0072; A61M 2205/581;A61M 1/0066; A61M 1/0025; A61M 1/0027; A61M 1/0031; A61M 1/0064; A61M 1/0041; A61M 3/0262; A61M 5/1424; A61M 5/1428; A61F 13/02; A61L 15/16
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Adam Marcetich

(57) ABSTRACT

A manually-activated reduced pressure treatment system includes a substantially rigid housing, and an end cap slidingly received by the housing. An inner chamber is disposed between the end cap and housing, and a volume of the inner chamber is variable in amount depending on the position of the end cap within the housing. The end cap is slidingly movable between an uncompressed position at which the volume of the inner chamber is at a maximum value and a compressed position at which the volume of the inner chamber is at a minimum value. A position indicating member is associated with the end cap and housing to
(Continued)

indicate the position of the end cap relative to the housing at predetermined positions between the uncompressed position and the compressed position.

21 Claims, 7 Drawing Sheets

Related U.S. Application Data division of application No. 11/974,534, filed on Oct. 15, 2007, now Pat. No. 8,007,257.

(60) Provisional application No. 60/851,494, filed on Oct. 13, 2006.

(52) U.S. Cl.
CPC ........ *A61M 1/0072* (2014.02); *A61M 3/0262* (2013.01); *A61M 27/00* (2013.01); *A61M 2205/581* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,376,868 A | 4/1968 | Mondiadis | |
| 3,520,300 A | 7/1970 | Flower, Jr. | |
| 3,568,675 A | 3/1971 | Harvey | |
| 3,602,387 A * | 8/1971 | Patnaude | B05B 11/3035 137/854 |
| 3,648,692 A | 3/1972 | Wheeler | |
| 3,682,180 A | 8/1972 | McFarlane | |
| 3,779,243 A * | 12/1973 | Tussey | A61M 1/0011 604/133 |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,278,089 A | 7/1981 | Huck et al. | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,828,546 A | 5/1989 | McNeil et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,102,404 A | 4/1992 | Goldberg et al. | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,718,355 A | 2/1998 | Garby et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,648,862 B2 | 11/2003 | Watson | |
| 6,814,079 B2 | 11/2004 | Heaton et al. | |
| 6,936,037 B2 | 8/2005 | Bubb et al. | |
| 7,004,915 B2 | 2/2006 | Boynton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2006/0229586 A1 | 10/2006 | Faries | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |

(56) References Cited

FOREIGN PATENT DOCUMENTS

| | | |
|---|---|---|
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 02-261472 | 10/1990 |
| JP | 4129536 | 4/1992 |
| JP | 2000-342679 A | 12/2000 |
| JP | 55-68370 B2 | 8/2014 |
| SG | 71559 | 4/2002 |
| WO | 80/02182 | 10/1980 |
| WO | 87/04626 | 8/1987 |
| WO | 88-04559 A1 | 6/1988 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 03-018098 A2 | 3/2003 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: " A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Ž ivadinovic, V. Dukić, D. Maksimovio, D. Radak, and P. Peška, "Vacuum Therapy in the Treatment of Peripheral Blood Vessels," Timok Medical Journal 11 (1986), pp. 161-164 (copy and certified translation).
F.E. E Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

REDUCED PRESSURE DELIVERY SYSTEM HAVING A MANUALLY-ACTIVATED PUMP FOR PROVIDING TREATMENT TO LOW-SEVERITY WOUNDS

CROSS-REFERENCE TO RELATED APPLICATIONS

This application is a continuation of U.S. patent application Ser. No. 13/205,807, filed Aug. 9, 2011, which is a divisional of U.S. patent application Ser. No. 11/974,534, filed Oct. 15, 2007, now U.S. Pat. No. 8,007,257 which claims the benefit of U.S. Provisional Application No. 60/851,494, filed Oct. 13, 2006, both of which are hereby incorporated by reference.

BACKGROUND OF THE INVENTION

1. Field of the Invention

The present invention relates generally to reduced pressure treatment systems and in particular to a reduced pressure treatment system having a manually-activated pump for providing treatment to low-severity wounds.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure has involved treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times.

While reduced pressure treatment is usually provided in a hospital or monitored-care setting, a great number of situations exist where it may be advantageous to provide reduced pressure therapy to ambulatory and other patients outside of these traditional settings. A conventional reduced pressure system includes an electrically-powered reduced pressure pump that requires a patient to remain relatively still during treatment. A need exists for a portable pump that is small in size and is capable of being manually-activated, and reactivated if necessary, by a patient receiving treatment.

SUMMARY

The problems presented in providing reduced pressure treatment to ambulatory patients and low-severity wounds are solved by the systems and methods of the present invention. A manually-activated reduced pressure treatment system is provided in accordance with an embodiment of the present invention. The system includes a substantially rigid housing, and an end cap slidingly received by the housing. An inner chamber is disposed between the end cap and housing, and a volume of the inner chamber is variable in amount depending on the position of the end cap within the housing. The end cap is slidingly movable between an uncompressed position at which the volume of the inner chamber is at a maximum value and a compressed position at which the volume of the inner chamber is at a minimum value. A position indicating member is associated with the end cap and housing to indicate the position of the end cap relative to the housing at predetermined positions between the uncompressed position and the compressed position.

In accordance with another embodiment of the present invention, a manually-activated reduced pressure system is provided and includes a reduced pressure manifold configured to be placed adjacent a tissue site. A manually-compressible pump in fluid communication with the reduced pressure manifold delivers a reduced pressure to the tissue site. The manually-compressible pump includes a flexible and compressible side wall and first and second end caps connected at opposite ends of the side wall. An inner chamber is defined by the side wall and the end caps, and the inner chamber includes a volume that varies from a maximum value when the side wall is in an uncompressed position to a minimum value when the side wall is in a compressed position. A connection port is disposed in one of the first and second end caps to allow fluid communication between the inner chamber and the reduced pressure manifold. A one-way valve is disposed in one of the first end cap, the second end cap, and the side wall to allow fluid expulsion from the inner chamber. A hydrophobic filter in communication with the one-way valve prevents liquids from exiting the inner chamber through the one-way valve, and an odor filter in communication with the one-way valve eliminates odors associated with gases expelled through the one-way valve.

In still another embodiment of the present invention, a method of activating a reduced pressure treatment pump is provided. The method includes manually compressing a flexible diaphragm to reduce a volume of a chamber fluidly connected to a tissue site. The method further includes audibly, visually, or tactilely indicating the positioning of the flexible diaphragm at a position between an uncompressed position and a compressed position. An estimated reduced pressure provided by the compressed flexible diaphragm is determined based on the indicated position, and the reduced pressure is delivered to the tissue site.

In yet another embodiment of the present invention, a low-profile reduced pressure treatment system includes a reduced pressure source and a reduced pressure manifold configured to be placed adjacent a tissue site. A substantially flat reduced pressure delivery tube is fluidly connected between the reduced pressure source and the reduced pressure manifold. The tube includes a substantially rectangular cross-section and a plurality of corrugations within the tube to prevent collapse of the tube during delivery of reduced pressure.

Other objects, features, and advantages of the present invention will become apparent with reference to the drawings and detailed description that follow.

DETAILED DESCRIPTION OF THE ILLUSTRATIVE EMBODIMENTS

In the following detailed description of the illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the illustrative embodiments are defined only by the appended claims.

Figure 1:
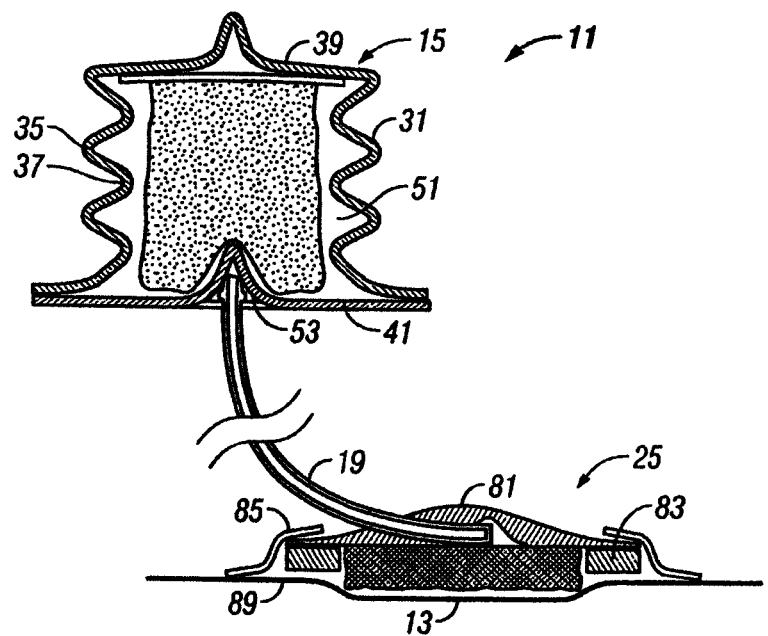
FIG. 1 illustrates a cross-sectional front view of a reduced pressure treatment system having a manually-compressible pump according to an embodiment of the present invention, the manually compressible pump being fluidly connected by a reduced pressure delivery tube to a reduced pressure manifold.
Figure 2:
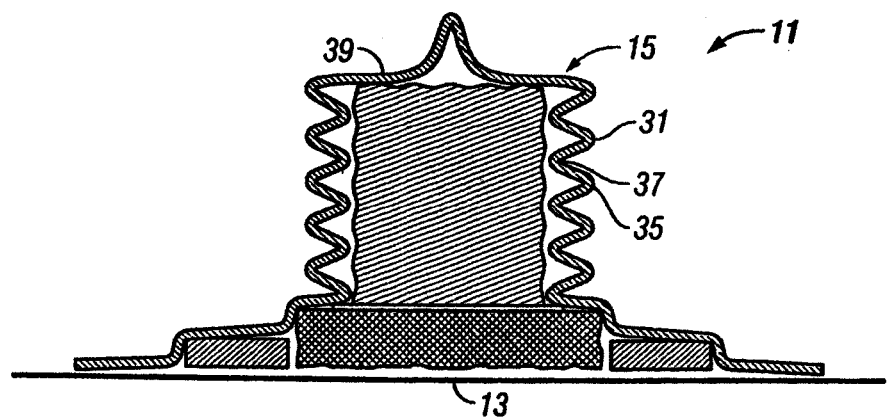
FIG. 2 depicts a cross-sectional front view of a reduced pressure treatment system having a manually-compressible pump according to an embodiment of the present invention, the manually compressible pump being fluidly connected to a reduced pressure manifold.
Figure 3:
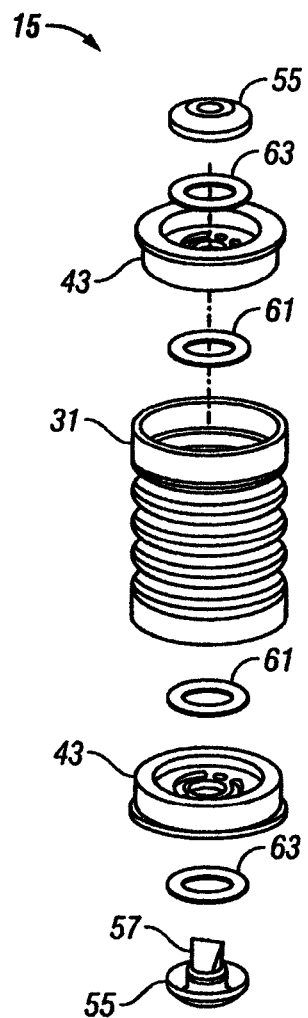
FIG. 3 illustrates an exploded perspective view of a manually-compressible pump according to an embodiment of the present invention.

Referring to FIGS. 1 and 3, a reduced pressure delivery system 11 according to an embodiment of the present invention is provided for administering a reduced pressure tissue treatment to a tissue site 13 of a patient. The reduced pressure delivery system includes a bellows pump 15 fluidly connected to a reduced pressure delivery tube 19, which is in turn fluidly connected to a low-profile wound dressing 25 (an integrated system that omits the reduced pressure delivery tube is illustrated in FIG. 2). The bellows pump 15 delivers a reduced pressure to the tissue site 13 through the reduced pressure delivery tube 19 and the dressing 25. The reduced pressure is maintained at the tissue site, which promotes micro-deformation of tissue at the tissue site and promotes growth of new tissue.

The bellows pump is preferably a cylindrically-shaped, manually operated pump that includes a corrugated side wall, or diaphragm 31. The corrugated side wall includes a plurality of ridges 35 and grooves 37 that facilitate compression of the bellows pump along its longitudinal axis. The bellows pump further includes a first end wall 39 and a second end 41 wall integrally connected at opposite ends of the corrugated side wall. Alternatively, the bellows pump may include first and second end caps, or valve caps 43 that are sealingly connected at opposite ends of the corrugated side wall (see FIG. 3). Together, the corrugated side wall and the opposing first and second end walls form a flexible bladder, the boundaries of which define an inner chamber 51. The volume of the inner chamber 51 is variable. In an uncompressed position, the corrugated wall of the bellows pump is in its naturally extended state (i.e. the corrugations are still present) and the volume of the inner chamber is at a maximum value. In a compressed position, the bellows pump has been subjected to a compressive force, thereby causing the volume of the inner chamber to decrease and the linear density of the corrugations to increase. When the corrugated wall is compressed, a biasing force is exerted by the corrugations to attempt to return the corrugated wall to the uncompressed position. Instead of corrugations, an independent biasing member, such as a spring, or the elasticity of a non-corrugated side wall, may be used to bias the side wall toward the uncompressed position.

A connection port 53 is preferably disposed on one of the end walls of the bellows pump to allow fluid connection of the inner chamber with the reduced pressure delivery tube. An umbrella valve 55 and a duck bill valve 57 are operably connected to the connection port to selectively admit or expel fluids from the inner chamber. The duck bill valve provides one-way fluid communication from the reduced pressure delivery tube to the inner chamber. The umbrella valve provides one-way fluid communication from the inner chamber to the ambient atmosphere surrounding the bellows pump. A similar umbrella valve is disposed within the end wall opposite the end wall containing the connection port.

Referring more specifically to FIG. 3, a hydrophobic filter 61 and an odor filter 63 (e.g. charcoal filter) are positioned near the umbrella valves. The hydrophobic filter prevents any liquids within the inner chamber from being expelled through the umbrella valve. The odor filter eliminates odors associated within any gases that are expelled from the inner chamber through the umbrella valves.

The plurality of valves associated with the bellows pump selectively allows fluid exchange with the inner chamber. When the bellows pump is initially primed to the compressed position (caused by exerting a manual compressive force on the end walls), the gaseous fluids within the inner chamber are expelled through one or both of the umbrella valves. The gaseous fluids pass through the odor filter prior to exiting the inner chamber. With the bellows in the compressed position, the corrugated wall, which has been elastically deformed, attempts to resume its uncompressed state. As the corrugated wall moves back toward its uncompressed state, the volume of the inner chamber increases, which results in a decrease in pressure within the inner chamber (the inner chamber acts as a closed system $P_1*V_1=P_2*V_2$). The differential pressure between the inner chamber and the ambient atmosphere (i.e. pressure at the tissue site) results in gaseous and liquid fluids from the reduced pressure delivery tube and the wound dressing being drawn into the inner chamber. This then results in a reduced pressure at the tissue site. With a properly sealed wound dressing, this reduced pressure can be maintained at the tissue site. The fluids drawn from the tissue site enter the inner chamber through the duck bill valve. The duck bill valve prevents these fluids from exiting the inner chamber.

One goal of the bellows device is to deliver and maintain a reduced pressure at the tissue site until the inner chamber becomes completely filled with liquid wound exudate. In some instances, the bellows pump may reach the uncompressed position (following initial priming) without the inner chamber being fully filled with wound exudate and other liquids. In this case, the bellows pump may be re-primed by again exerting a compressive force on the end walls of the bellows pump. As the volume of the inner chamber again decreases, gaseous fluids within the inner chamber are expelled through the umbrella valves. The hydrophobic filters prevent liquids within the inner chamber from being expelled. Because the bellows pump includes more than one umbrella valve, the pump can be re-primed regardless of its orientation.

The bellows pump may include an absorbent foam disposed within the inner chamber to capture wound exudate and other fluids that are removed from the tissue site. Additionally, a one-way membrane may be provided within the bellows pump to prevent any fluids from backflowing out of the inner chamber.

Figure 4:
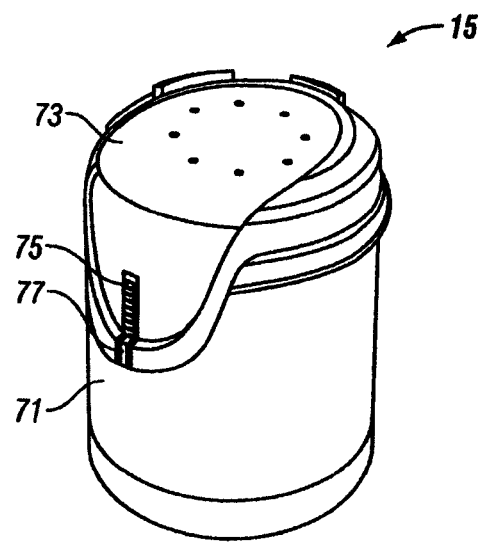
FIG. 4 depicts a perspective view of a manually-compressible pump according to an embodiment of the present invention.
Figure 5:
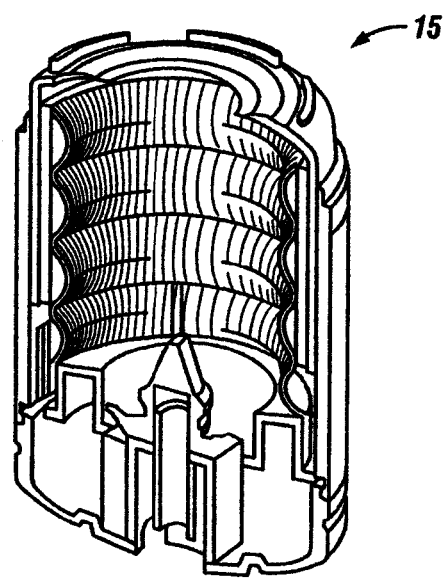
FIG. 5 illustrates a cross-sectional perspective view of the pump of FIG. 4.
Figure 6:
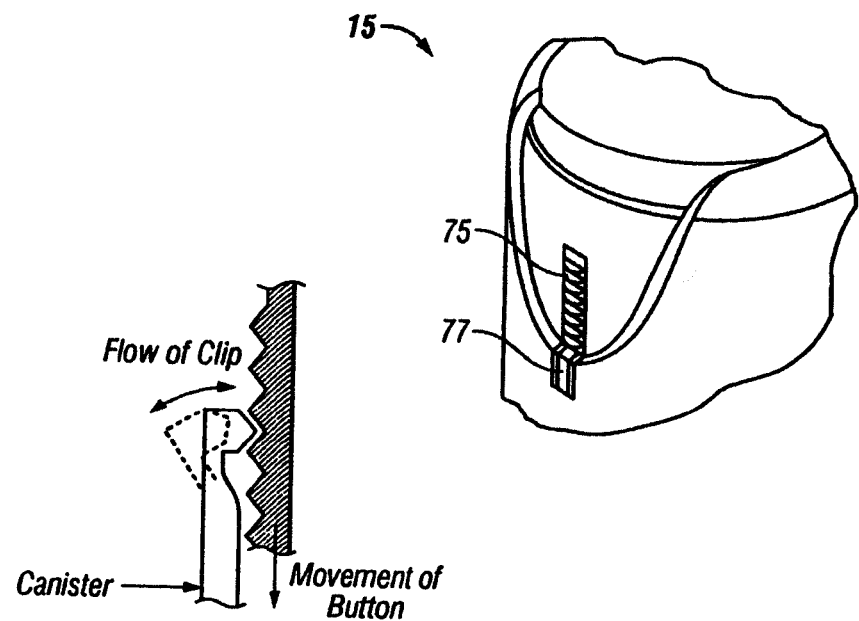
FIG. 6 depicts a perspective view of a position indicating member disposed on the manually-compressible pump of FIG. 4, the position indicating member having a plurality of teeth and a pawl.
Figure 7:
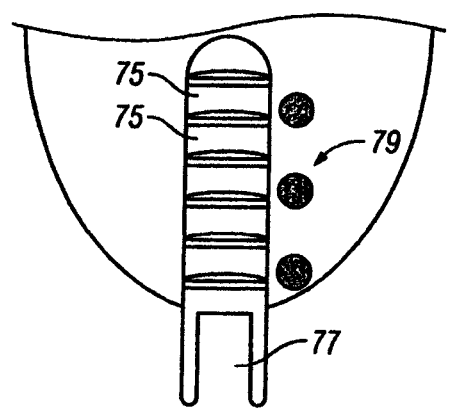
FIG. 7 illustrates a front view of the position indicating member of FIG. 6.

Referring to FIGS. 4 and 5, in one embodiment of the present invention, the bellows pump may include a rigid housing 71 that contains the corrugated wall. An end cap 73 may be slidingly carried by the housing and positioned over the corrugated wall such that the corrugated wall is compressed by pressing on the end cap. A position indicating member having a detent 75 and tab 77 may be operably associated with the housing and end cap to provide an audible and tactile "click" when the corrugated wall reaches the compressed position. Alternatively, and referring to FIGS. 6-8, a plurality of teeth or detents and a pawl may be operably associated with the housing and end cap to generate a ratcheting sound as the bellows pump is primed. Each individual "click" may be representative of a defined differential pressure that the bellows pump is capable of providing at that instant in time. The audible indicators may also be accompanied by a visual indicator 79 to convey to a user how much differential pressure will be provided.

Figure 8:
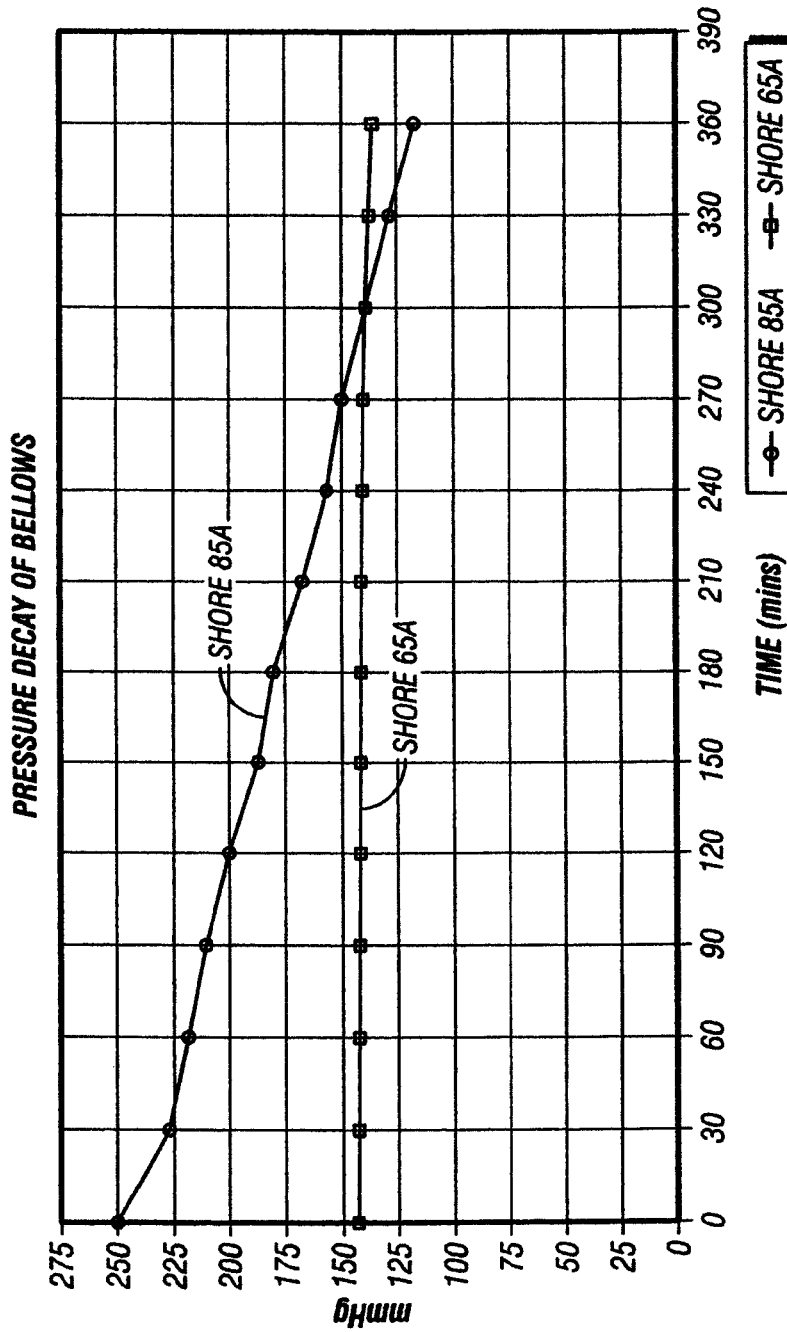
FIG. 8 depicts a graph of test results measuring the pressure decay over time of various manually-compressed bellows pumps having flexible walls of different hardness values.

Referring to FIG. 8, testing was performed to measure pressure decay associated with bellows pumps having corrugated walls made from materials of different hardness values. While the results indicate that a material having Shore 65 A experienced less decay, this is in part due to an improved seal at the wound dressing. The Shore 65 A material was found to be capable of providing between 125 and 150 mm Hg of differential pressure. These levels of pressure are capable of being maintained for at least six hours. For higher pressures, harder materials (such as the Shore 85A material) may be used. It is possible for pressures of 250 mm Hg, and possibly even above 400 mm Hg to be generated using this type of pump design.

It should be noted that while a bellows pump is described, any manually operated pump, including without limitation a diaphragm pump or a piston pump may be substituted for the bellows pump. In some situations, it may be desired to prime (or set) the pump using electrical power, but in most cases, the pump will be capable of manual operation by the user without electrical power.

Referring again to FIG. 1, the low-profile wound dressing includes a tube connector 81, a hydrogel ring 83, and a film 85. The tube connector is positioned above a reduced pressure manifold such that an aperture of the tube connector is in fluid communication with the manifold. The hydrogel ring is disposed between the tube connector and a tissue surface 89 of the patient adjacent the tissue site. The film, preferably made of polyurethane, is adhesively applied to the tube connector and the tissue surface of the patient to secure the dressing against the patient and provide a seal between the dressing and the patient. The sealing characteristics of the dressing are further enhanced by the hydrogel ring, which not only seals against the tissue surface of the patient, but also prevents the tissue surface from becoming damaged during use of the dressing.

The manifold is preferably a highly reticulated, open-cell foam. The manifold allows distribution of the reduced pressure provided by the bellows pump. It should be noted that any material capable of distributing reduced pressure could be used in place of the open-cell foam.

Figure 9:
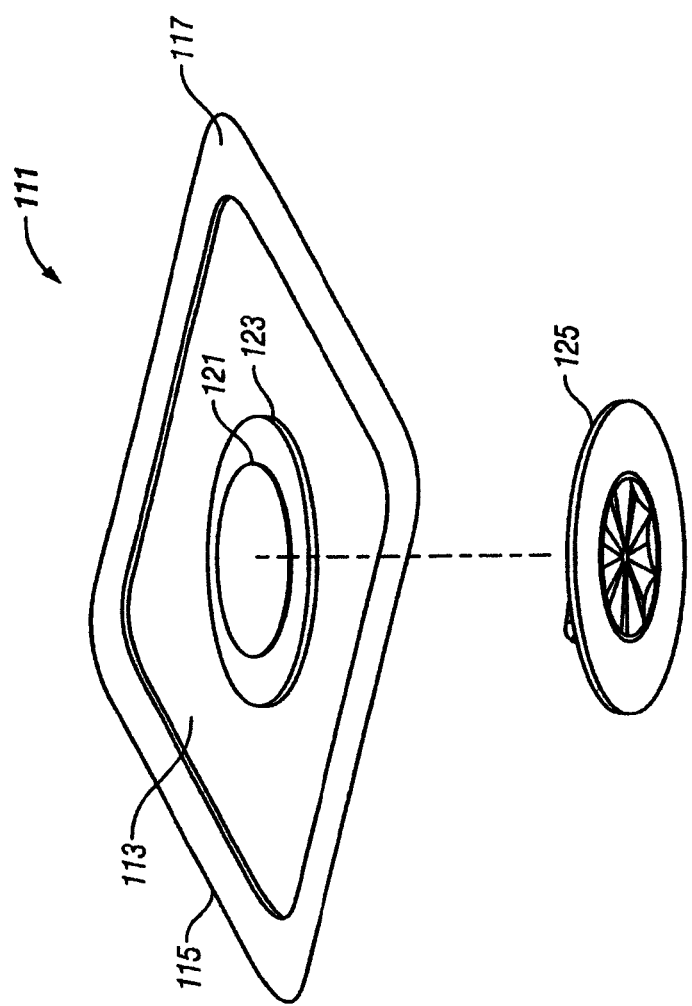
FIG. 9 illustrates a reduced pressure dressing having an adhesive film, a hydrogel, and a tube connector according to an embodiment of the present invention.

Referring to FIG. 9, an integrated wound dressing 111 may also be used with the reduced pressure delivery system. The integrated wound dressing includes a large island of a hydrogel 113 disposed on a film 115. The film preferably includes an adhesive 117 to serve as a backup seal to the hydrogel. An aperture 121 is disposed in the film and an aperture 123 is disposed in the hydrogel to allow through connection of a conformable tube connector 125.

Figure 10:
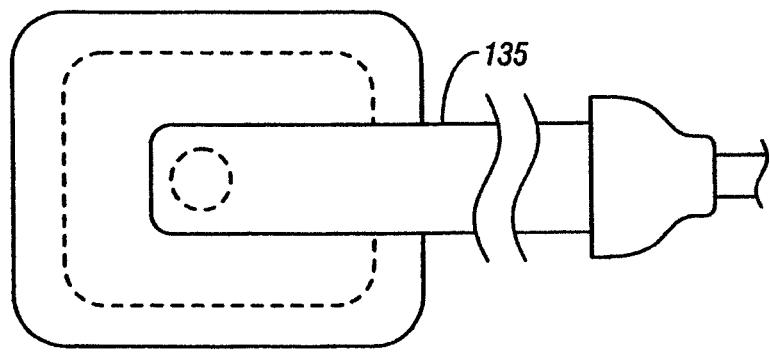
FIG. 10 depicts a top view of the reduced pressure dressing of FIG. 9 fluidly connected to a low-profile reduced pressure delivery tube.
Figure 11:
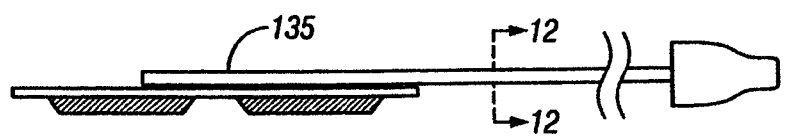
FIG. 11 illustrates a side view of the reduced pressure dressing and reduced pressure delivery tube of FIG. 10.
Figure 12:
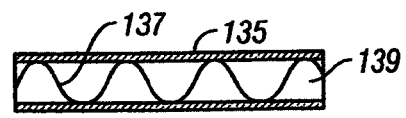
FIG. 12 depicts a cross-sectional view of the reduced pressure delivery tube of FIG. 10.

Referring to FIGS. 10-12, in another embodiment of the wound dressing, an ultra-low-profile reduced pressure delivery tube 135 is directly connected to the dressing. The tube is fairly flat and rectangular in cross section, which significantly reduces the thickness of the overall dressing when connected to the tube. Preferably, corrugations 137 are provided within the tube (see FIG. 12) to resist collapse of the tube under pressure. The tube and corrugations may be extruded together in a single manufacturing process, or may be assembled following separate manufacturing processes. A plurality of flow channels 139 are defined between the corrugations. The tube is preferably connected to the film by pouring a hydrogel over the film and tube and causing it to gel.

It should be apparent from the foregoing that an invention having significant advantages has been provided. While the invention is shown in only a few of its forms, it is not just limited but is susceptible to various changes and modifications without departing from the spirit thereof.

What is claimed is:

1. A manually-compressible pump for reduced pressure treatment, comprising:
   a compressible side wall;
   first and second end caps connected at opposite ends of the side wall to form an inner chamber defined by the side wall and the end caps, the inner chamber having a volume that varies from a maximum value when the side wall is in an uncompressed position to a minimum value when the side wall is in a compressed position;
   a connection port disposed in one of the first and second end caps to allow fluid communication with the inner chamber;
   a one-way valve disposed in one of the first end cap, the second end cap, and the side wall to allow fluid expulsion from the inner chamber; and
   a hydrophobic filter in communication with the one-way valve to prevent liquid from exiting the inner chamber through the one-way valve.

2. The pump of claim 1, further comprising an odor filter in communication with the one-way valve to eliminate odors associated with fluid expelled through the one-way valve.

3. The pump of claim 1, wherein the side wall comprises a plurality of corrugations configured to bias the side wall toward the uncompressed position.

4. The pump of claim 1, wherein the side wall includes a plurality of ridges and grooves configured to bias the side wall toward the uncompressed position.

5. The pump of claim 1, further comprising a spring configured to bias the side wall toward the uncompressed position.

6. The pump of claim 1, wherein the one-way valve is disposed in the first end cap.

7. The pump of claim 6, further comprising a second one-way valve disposed in the second end cap.

8. The pump of claim 1, further comprising an absorbent foam disposed within the inner chamber.

9. The pump of claim 1, further comprising:
a housing that contains the side wall; and
a position indicating member associated with the housing and at least one of the end caps to indicate a position of the side wall at predetermined positions between the uncompressed position and the compressed position.

10. The pump of claim 9, wherein the position indicating member comprises a plurality of teeth and a pawl configured to mate with one another to indicate the position of the side wall at predetermined positions between the uncompressed position and the compressed position.

11. The pump of claim 9, wherein the position indicating member provides an audible indication of the end cap being moved from the uncompressed position toward the compressed position.

12. A pump for reduced pressure therapy, the pump comprising:
a bellows defining an inner chamber having a variable volume;
a connection port configured allow fluid communication between the inner chamber and a delivery tube;
a one-way valve configured to allow fluid expulsion from the inner chamber; and
a hydrophobic filter in communication with the one-way valve to prevent liquid from exiting the inner chamber through the one-way valve.

13. The pump of claim 12, wherein the bellows comprises a corrugated side wall.

14. The pump of claim 12, further comprising a second one-way valve configured for fluid communication from the delivery tube to the inner chamber.

15. The pump of claim 12, further comprising a second one-way valve configured to allow fluid expulsion from the inner chamber.

16. The pump of claim 12, further comprising:
a housing containing the bellows; and
a position indicating member associated with the housing to indicate predetermined positions of the bellows.

17. The pump of claim 12, further comprising:
a housing containing the bellows;
an end cap slidingly carried by the housing and positioned over the bellows;
a position indicating member operably associated with the housing and the end cap to indicate the position of the end cap relative to the housing at predetermined positions between an uncompressed position and a compressed position.

18. The pump of claim 17, wherein the position indicating member comprises a plurality of teeth and a pawl configured to mate with the plurality of teeth.

19. The pump of claim 12, wherein the bellows comprises:
a corrugated side wall; and
a first end wall and a second end wall connected at opposite ends of the corrugated side wall.

20. The pump of claim 19, wherein:
the connection port is disposed in the first end wall; and
the one-way valve is disposed in the second end wall.

21. The pump of claim 20, further comprising:
a second one-way valve disposed in the first end wall configured to allow fluid expulsion from the inner chamber;
a third one-way valve configured for fluid communication from the delivery tube to the inner chamber;
a housing containing the bellows;
an end cap slidingly carried by the housing and positioned over the second end wall; and
a plurality of teeth and a pawl operably associated with the housing and the end cap to indicate the position of the end cap relative to the housing at predetermined positions between an uncompressed position and a compressed position.

* * * * *